United States Patent
Khoja et al.

(10) Patent No.: US 10,781,439 B2
(45) Date of Patent: Sep. 22, 2020

(54) EXTRACTION OF CFDNA FROM BIOLOGICAL SAMPLES

(71) Applicant: Covaris, Inc., Woburn, MA (US)

(72) Inventors: Hamid Khoja, Rancho Santa Margarita, CA (US); Hans-Ulrich Thomann, Stow, MA (US); James A. Laugharn, Jr., Boston, MA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 15/473,672

(22) Filed: Mar. 30, 2017

(65) Prior Publication Data

US 2017/0283788 A1  Oct. 5, 2017

Related U.S. Application Data

(60) Provisional application No. 62/315,341, filed on Mar. 30, 2016.

(51) Int. Cl.
*C12N 15/10* (2006.01)
*C12N 13/00* (2006.01)

(52) U.S. Cl.
CPC ......... *C12N 15/1003* (2013.01); *C12N 13/00* (2013.01)

(58) Field of Classification Search
CPC . C12N 15/1003; C12N 13/00; A61K 38/1761
See application file for complete search history.

(56) References Cited

U.S. PATENT DOCUMENTS

| | | | | |
|---|---|---|---|---|
| 8,969,058 B2 * | 3/2015 | Stone | ............... | G01N 1/405 204/157.15 |
| 2008/0131954 A1 * | 6/2008 | Stone | ............... | C12N 15/1006 435/270 |
| 2015/0111208 A1 * | 4/2015 | Umbarger | ............... | C12Q 1/6883 435/6.11 |
| 2016/0022976 A1 * | 1/2016 | Peyman | ............... | A61K 9/0009 600/439 |

FOREIGN PATENT DOCUMENTS

| | | | |
|---|---|---|---|
| CN | 105 087 789 A | | 11/2015 |
| WO | WO 2016/011075 | * | 1/2016 |
| WO | WO 2016/073353 | * | 5/2016 |
| WO | WO 2016/145039 | * | 9/2016 |
| WO | WO 2016/176131 A1 | | 11/2016 |

OTHER PUBLICATIONS

Potluri, Improving DNA Quality using FFPE tissues for Array Comparative Genomic Hybridization to find Single Nucleotide Polymorphisms (SNPs) in Melanoma, 2015, Thesis, pp. 1-100, publicly availbel on Jul. 22, 2015. (Year: 2015).*
Snyder et al, Cell-free DNA Comprises an In Vivo Nucleosome Footprint that Informs its Tissues-of-Origin, 2016, cell 164,57-68, published on Jan. 14, 2016. (Year: 2016).*
Lane et al, Extracellular vesicles as circulating cancer biomarkers: opportunities and challenges, 2018, Clin Trans Med, 7:14, pp. 1-11 (Year: 2018).*
Khoja et al, Chromatin Shearing Based on Covaris Adaptive Focused Acoustics (AFA), 2009, poster presentation, p. 1 (Year: 2009).*
Khoja et al, Chromatin Shearing Based on Covaris Adaptive Focused Acoustics (AFA), 2009, poster presentation, p. 1, publication date support document, p. 1 (Year: 2009).*
Kumar et al, Chromatin Immunoprecipitation Assay and its Variants for the Analysis of DNA-Protein Interactions, 2016, Asian Journal of Science and Technology, 7, 3074-3081 (Year: 2016).*
Wilson et al , Universal Sample Processing of Multiple Sample Types for Reproducible Proteomic Sample Preparation, poster presentation, 2018 p. 1 (Year: 2018).*
Invitation to Pay Additional Fees for International Application No. PCT/US2017/024944, dated Jun. 26, 2017.
[No Author Listed], truXTRAC™ cfDNA for Plasma—Column Purification Kit (24). Adaptive Focused Acoustics (AFA)-Based DNA Extraction & Column-Based Purification of Circulating Cell-Free DNA (cfDNA). Product PN 520234. Covaris. http://covarisinc.com/wp-content/uploads/pn_010382.pdf. 14 pages [last accessed Jun. 7, 2017].
Devonshire et al., Towards Standardisation of Cell-Free DNA Measurement in Plasma: Controls for Extraction Efficiency, Fragment Size Bias and Quantification. Analytical and Bioanalytical Chemistry. May 24, 2014;406(26):6499-6512.
Schwarzenbach et al., Cell-Free Nucleic Acids as Biomarkers in Cancer Patients. Nature Reviews Cancer. May 12, 2011;11(6):426-437.
Wang et al., Cell Lysis by Low Power Focused Acoustic Transducer and Investigation of Acoustic Intensity Threshold for Cytolysis of Various Cell Lines. 15th International Conference on Miniaturized Systems for Chemistry and Life Sciences. http://www.rsc.org/images/LOC/2011/PDF/Papers/146_0871.pdf. Oct. 6, 2011:434-436.
International Search Report and Written Opinion for International Application No. PCT/US2017/024944, dated Sep. 7, 2017.

* cited by examiner

*Primary Examiner* — Narayan K Bhat
(74) *Attorney, Agent, or Firm* — Wolf, Greenfield & Sacks, P.C.

(57) ABSTRACT

Focused acoustic treatment of samples including a target biomolecule, such as cfDNA, may aid in the recovery of the biomolecule from a sample. cfDNA in a sample, whether chemically stabilized or not, may be linked or otherwise bound to histones or other proteins, e.g., by hydrogen bonds of histones or chaperone proteins to DNA and/or covalent crosslinks of such proteins to the DNA. Focused acoustic energy may remove or disrupt such links, aiding in isolation of the cfDNA from the sample.

17 Claims, 5 Drawing Sheets

EXTRACTION OF CFDNA FROM BIOLOGICAL SAMPLES

CROSS REFERENCE TO RELATED APPLICATION

This application claims the benefit of U.S. Provisional Application No. 62/315,341, filed Mar. 30, 2016, which is hereby incorporated by reference in its entirety.

BACKGROUND

1. Field of the Invention

Systems and methods for processing of samples with acoustic energy are generally disclosed.

2. Related Art

Acoustic energy-based sample processing devices, such as Adaptive Focused Acoustic (AFA) apparatuses made by Covaris of Woburn, Mass., are effective for homogenization and disruption of biological tissues, cells, and other sample material. With such devices, a controlled acoustic field enables repeatable processes to be developed which often result in higher recovery of target molecules as compared to bath and probe sonicators, blade homogenizers, and bead beaters. Such target molecules may be, for example, DNA, RNA, or proteins.

SUMMARY OF INVENTION

Detection and/or quantitation of certain biomarkers such as cell free DNA (cfDNA) in biological samples like blood, saliva, sputum, stool, urine, or tissue can help to diagnose disease, establish a prognosis, and/or aid in selecting or monitoring treatment. For example, the concentration of certain genetic markers in cfDNA can indicate cancer progression or treatment success, and can have utility in noninvasive prenatal testing (NIPT) for the detection of trisomy or monosomy, as well as short insertion and deletion mutations in an unborn child (J. Clin. Med. 2014, 3, 537-565; doi:10.3390/jcm3020537). Also, relative concentrations (or profiles) of specific metabolites or RNAs in venous blood samples can indicate increased risk of conditions such as insulin resistance or obstructive coronary artery disease (Cobb et al (2013) A Novel Fasting Blood Test for Insulin Resistance and Prediabetes. J Diabetes Sci Technol 2013; 7(1):100-110; Rosenberg et al (2010) Multicenter Validation of the Diagnostic Accuracy of a Blood-Based Gene Expression Test for Assessing Obstructive Coronary Artery Disease in Nondiabetic Patients. Ann Intern Med. 2010; 153(7):425-434). Specific changes in the sequence or modifications of certain DNAs present in stool samples can indicate the presence of colon cancer (Imperiale et al (2014) Multitarget Stool DNA Testing for Colorectal-Cancer Screening. N Engl J Med 2014; 370:1287-1297), and the presence of viral proteins or RNAs in dried blood spots can allow diagnosis of infectious diseases such as AIDS. cfDNA is also becoming increasingly important as a marker for early detection of transplant/allograft rejection, since the cfDNA that is shed from donor tissue is readily identifiable by donor-specific genetic sequence variations (De Vlaminck et al. (2013) Circulating Cell-Free DNA Enables Noninvasive Diagnosis of Heart Transplant Rejection. Sci Transl Med 6(241): 241ra77; Snyder et al. (2011) Universal noninvasive detection of solid organ transplant rejection. Proc Natl Acad Sci USA 108(15):6229-6234).

A pre-requisite for successful use of biological samples in biomarker assays is the ability to efficiently and reproducibly extract cfDNA from stabilized, or non-stabilized, biological samples in amounts sufficient for the intended analysis, while simultaneously preserving the integrity and the original composition/content of the cfDNA in the matrix of interest. One example is the extraction of cfDNA from blood. Current methods for the extraction of cfDNA from whole blood involves the chemical stabilization of the whole blood at the time of collection with fixatives that prevent the lysis of leukocytes, thereby significantly reducing the release of contaminating genomic DNA and mitochondrial DNA into the serum and preserving the starting concentration and composition of cfDNA in the blood sample. Studies have indicated that the majority of cfDNA in such chemically stabilized samples are likely histone bound or otherwise linked to chaperone proteins, shielding the DNA from rapid degradation and pathophysiological effects. In addition cfDNA may be associated with apoptotic bodies (Schwarzenbach et al. (2013) Circulating nucleic acids as biomarkers in breast cancer. Breast. Cancer Res 15:211-229). For example, the stabilizer in Streck blood collection tubes (BCTs) used to collect and stabilize whole blood samples employ either formaldehyde, or formaldehyde-releasing agents which stabilize leukocytes as well as red blood cells, thereby significantly reducing cell lysis. The fixative also likely fixes and covalently links DNA to histones, other associated proteins and peptides, which are highly abundant in plasma (Anderson and Anderson (2002). The Human Plasma Proteome. Mol Cell Proteomics 1(11): 845-867), thereby further complicating the extraction and purification of cfDNA-histone complexes, and further complicating the efficient extraction and purification of cfDNA because parts of the DNA may still be associated with histone complexes and therefore must be separated from histones and other bound materials prior to analysis.

In some embodiments, methods in accordance with aspects of the invention provide for improved stabilization of various biomarkers within diverse biological samples and/or for improved extraction of intact biomarker molecules from certain stabilized or non-stabilized biological samples. Aspects of the invention provide a method and/or system for the efficient extraction and purification of cfDNA from a sample such as a blood, saliva, sputum, urine, stool, or tissue. In some embodiments, focused acoustic energy may be employed to aid in the release of cfDNA from linked histones, other proteins and/or apoptotic bodies, without compromising the integrity and original sequence content of the target biomarker with regard to the downstream analysis method. For example, focused acoustic energy may be used to enhance the reverse crosslinking rate of the histones from cfDNA, or otherwise release or disrupt covalent and/or non-covalent bonds between the cfDNA and histones or other proteins, or release cfDNA associated with apoptotic bodies. While this will result in increasing the overall cfDNA yield, it will also ensure that the complexity of the extracted cfDNA is reflective of the original content in the sample, which cannot be guaranteed if using other methods that solely rely on proteolytic degradation and chaotropic solubilization/dissociation of proteins. Focused acoustic energy may also, or alternatively, be applied after reverse crosslinking of covalent bonds between proteins and nucleic acids that were introduced by preservative agents (e.g., formalin and other crosslinking agents), since nucleic acid may still be bound non-covalently and be entangled in protein complexes and general debris.

Other aspects of the invention provide a method and/or system for extracting biomarkers such as cfDNA or other nucleic acids, proteins, metabolites, exosomes, etc. from a sample such as a blood, saliva, sputum, urine, stool, or tissue, in stabilized or non-stabilized form. In some embodiments, focused acoustic energy may be used to break down mammalian or bacterial cells without addition of chemicals to liberate biomarkers. In another example, focused acoustic energy may be used to selectively lyse cells such as red or white blood cells in a blood sample, while leaving relatively smaller exosomes unharmed Such differential treatment using fine-tuned focused acoustic energy may provide a sample that is particularly useful for analysis of the exosomes in the sample. In another example, focused acoustic energy can be used to break down mucopolysaccharides in samples such as sputum or saliva to reduce the sample viscosity, homogenizing the sample and making target biomarkers within the sample more accessible. In another example, focused acoustic energy may be used to enhance release of biomarkers from stabilized samples such as dried blood spots or FFPE-tissue (formalin fixed, paraffin embedded tissue) by dissociating biomarkers from the stabilization matrix and simultaneously promoting sample re-hydration.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Figure 1:
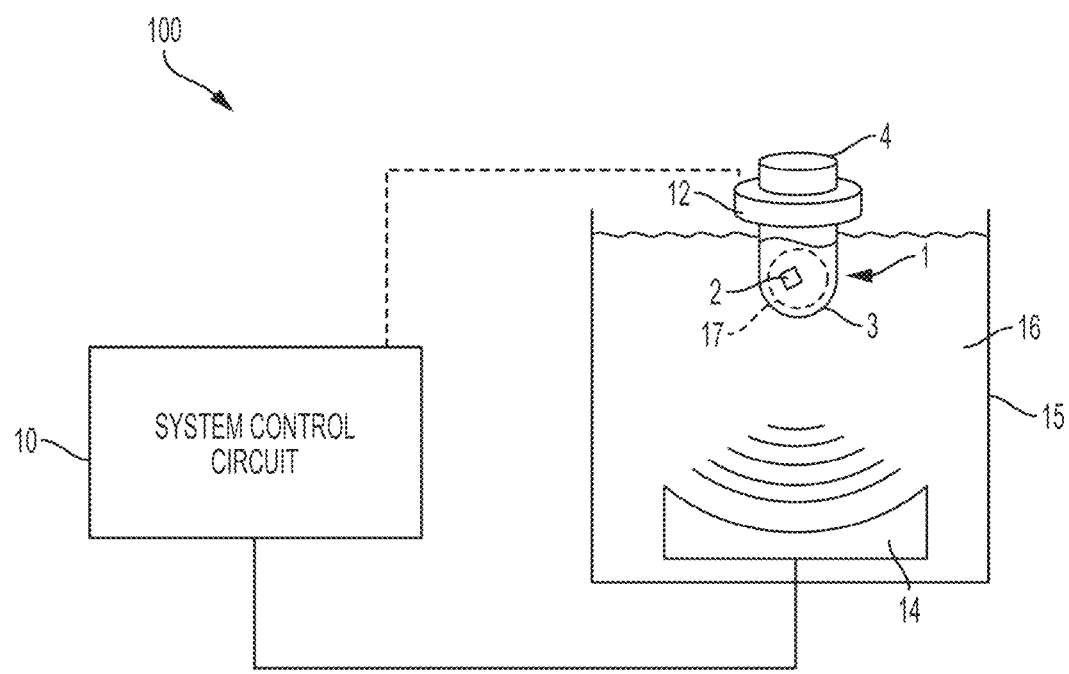
FIG. 1 shows a schematic block diagram of an acoustic treatment system that incorporates one or more aspects of the invention.

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

FIG. 1 shows a schematic block diagram of an acoustic treatment system 100 that incorporates one or more aspects of the invention and/or can be employed with one or more aspects of the invention. It should be understood that although embodiments described herein may include most or all aspects of the invention, aspects of the invention may be used alone or in any suitable combination with other aspects of the invention. In this illustrative embodiment, the acoustic treatment system 100 includes an acoustic energy source with an acoustic transducer 14 (e.g., including one or more piezoelectric elements) that is capable of generating an acoustic field (e.g., at a focal zone 17) suitable to cause mixing, e.g., caused by cavitation, and/or other effects in a sample 1 contained in a vessel 4. The sample 1 may include "solid" particles, such as cells, or other material 2, such as cell-free DNA or other nucleic acid material, and/or liquid 3, such as blood serum, water, etc. Under the control of a control circuit 10 (described in more detail below), the acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control. The focal zone may be stationary relative to the sample, or it may move relative to the sample.

In some embodiments, the transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response may be linear if not overdriven. The high-energy focus zone 17 of one of these domes is typically cigar-shaped. At 1 MHz, the focal zone 17 is about 6 cm long and about 2 cm wide for a 20 cm dome, or about 15 mm long and about 3 mm wide for a 10 cm dome. The peak positive pressure obtained from such systems at the focal zone 17 is about 1 MPa (mega Pascal) to about 10 MPa pressure, or about 150 PSI (pounds per square inch) to about 1500 PSI, depending on the driving voltage. The focal zone 17, defined as having an acoustic intensity within about 6 dB of the peak acoustic intensity, is formed around the geometric focal point. It is also possible to generate a line-shaped focal zone, e.g., that spans the width of a multi-well plate and enables the system 1 to treat multiple wells simultaneously.

To control an acoustic transducer 14, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. Moreover, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others. Thus, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The vessel 4 may have any suitable size or other arrangement, e.g., may be a glass or metal tube, a plastic container, a well in a microtiter plate, a vial, or other, and may be supported at a location by a vessel holder 12. Although a vessel holder 12 is not necessarily required, the vessel holder 12 may interface with the control circuit 10 so that the vessel 4 and the sample in the vessel is positioned in a known location relative to an acoustic field, for example, at least partially within a focal zone of acoustic energy. In this embodiment, the vessel 4 is a borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

In accordance with an aspect of the invention, focused acoustic energy may be used dislodge histones and other chaperone proteins from cfDNA, thereby increasing not only the yield of the cfDNA after purification, but also the complexity of the sample. In one example experiment regarding extraction of cfDNA from a sample, the inventors obtained blood samples collected directly into Streck BCTs. The stabilizing agent contained in the Streck BCTs included proprietary fixatives including either formaldehyde, or formaldehyde releasing agents, to fix leukocytes and red blood cells (RBC), preventing their lysis. Once the blood samples were obtained, the red blood cells and leukocytes were separated and removed from plasma utilizing a double centrifugation strategy in which the blood samples were centrifuged at 3000 g for 10 minutes and the platelet-deprived plasma transferred to another tube. The centrifugation was repeated on the plasma sample for an additional 5 minutes, to remove any residual cells carried through from the first centrifugation. The platelet-deprived plasma was then aliquoted into several tubes for carrying out an energy course extraction with focused acoustic energy to determine optimal processing energies required to release cfDNA from protein without damaging the cfDNA. After focused acoustic energy extraction, the cfDNA was purified using a magnetic bead-based purification kit from BioO (NextPrep-Mag-cfDNA isolation kit).

Figure 2:
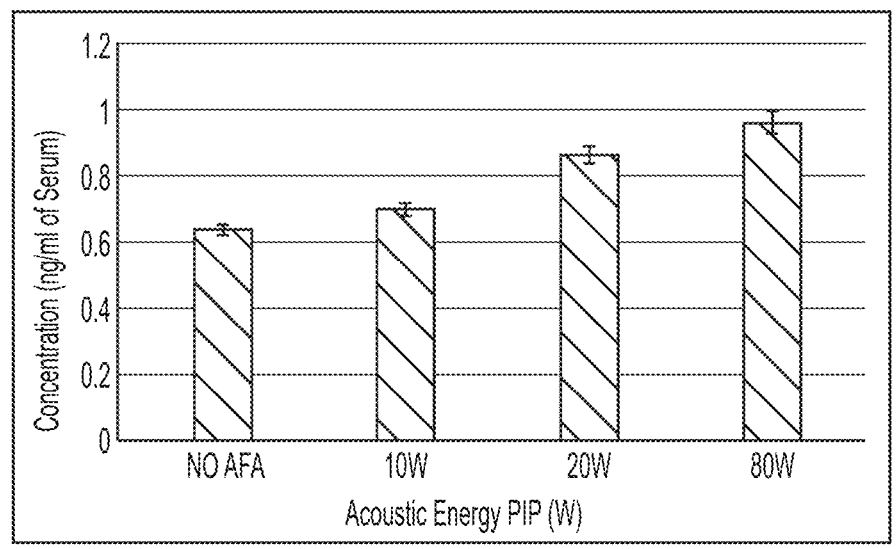
FIG. 2 shows isolated cfDNA concentrations resulting after different acoustic treatments.

The protocol for the focused acoustic energy sample processing involved transferring 1 ml aliquots of the platelet-deprived plasma to a Covaris 1 ml milliTUBE, and then exposing the plasma samples to focused acoustic energy in a Covaris S220 using different focused acoustic energy power settings. Generally speaking, the focused acoustic energy was provided with a 5% duty cycle, 10-80 W Peak Incidence Power (PIP), and 50 cycles per burst for a 120 second processing time per sample. In these examples, the PIP was varied between 10-80 W, but it is expected that other PIP settings may be successfully employed, as well as higher duty factor settings and/or shorter time periods for treatment such as 5-20 seconds of focused acoustic energy. Other variations in focused acoustic energy parameters may be employed to suitably dislodge or disrupt the bond or link between histones and/or other proteins with the cfDNA. For example, the acoustic energy may disrupt the hydrogen binding of histones or chaperone proteins to DNA, and/or reverse the covalent crosslinks with these proteins caused as a result of a stabilization process. The processed samples were then incubated at 56C in the presence of proteinase K, and magnetic beads for 15 minutes. The beads were then pulled down using a magnet, and the beads then sequentially washed in two different wash buffers. The DNA was then eluted in 60 μl of elution buffer. The purification can also be achieved using any other commercially available cfDNA kit such as the Covaris truXTRAC-cfDNA from Plasma kit. DNA concentration was determined using a high sensitivity Qubit assay. FIG. 2 shows the concentration of cfDNA for three different focused acoustic energy power (PIP) settings, i.e., 10, 20 and 80 W, as well as a sample that was not treated with focused acoustic energy. In all samples, the acoustic energy had a 5% duty cycle, and was set to 50 cycles per burst (CPB) for a 120 second treatment time.

Yield analysis of the extracted cfDNA indicated a correlated response with focused acoustic energy dose such that the total DNA yield from the serum samples increased with increasing focused acoustic energy power. Thus, focused acoustic energy was shown to enhance extraction of cfDNA at least in comparison to the use of no focused acoustic energy. In order to determine whether the increase in the DNA yield was due to lysis of contaminating blood cells that were still present in double-spun plasma, or (as was expected) due to enhanced release of cfDNA from histones, chaperone proteins, and/or apoptotic bodies, qPCR reactions were performed as published by Lin et al. (2009. High-quality genomic DNA extraction from formalin-fixed and paraffin-embedded samples deparaffinized using mineral oil. Anal Biochem 395(2): 265-267), utilizing two primer pairs targeting the human actin gene: one primer pair amplifies a 67 bp (short), and the other a 411 bp (long) amplicon. Short amplicon primers will amplify the target from cfDNA that is presented as small (nucleosomal-derived) 150-180 bp fragments as well as in the larger (higher molecular weight) fragments. In contrast, long amplicon primers will only amplify targets that are longer than 411 bp and that are represented in cfDNA that is stemming from necrotic cell death or DNA that was released from contaminating blood cells that may have been lysed during acoustic treatment. High molecular weight DNA fragments, i.e. fragments greater than 500 bp in length, that are present in a cfDNA isolate may be originating from necrotic cell death events. A recent comparison of cfDNA purification methods show the shortcomings of existing extraction methods that bias the yield towards small (low molecular weight) nucleosomal size fragments (Perez-Barrios et al. (2016). Comparison of methods for circulating cell-free DNA isolation using blood from cancer patients: impact on biomarker testing. Transl Lung Cancer Res 5(6):665-672). Thus, cfDNA isolation methods should be as inclusive as possible to avoid that the ratios of existing DNA compositions in plasma samples are not altered during isolation and purification (Devonshire et al. (2014). Towards standardization of cell-free DNA measurement in plasma: controls for extraction efficiency, fragment size bias and quantification. Anal Biochem Chem 406:6499-6512).

Figure 3:
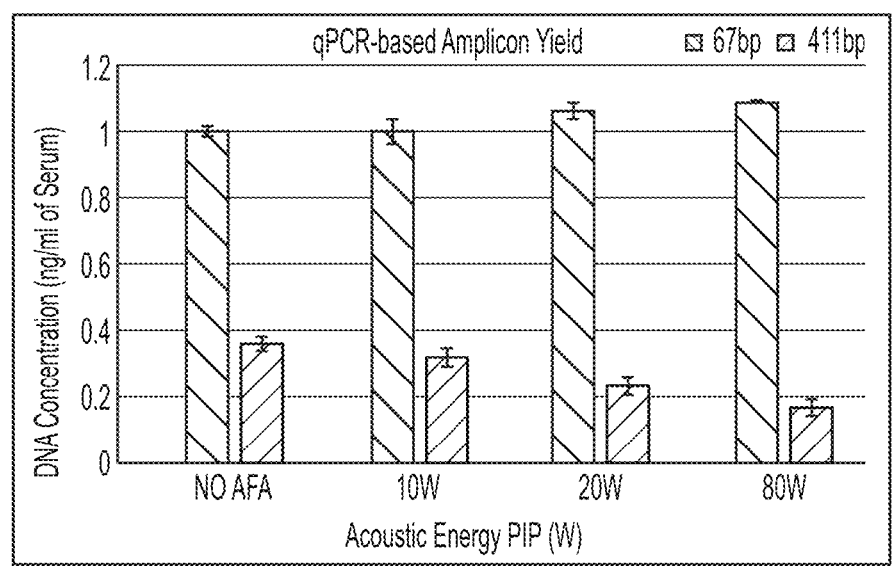
FIG. 3 shows a q-PCR amplicon yield used to test whether acoustic energy treatment resulted in cfDNA/histone or other protein bond disruption.
Figure 4:
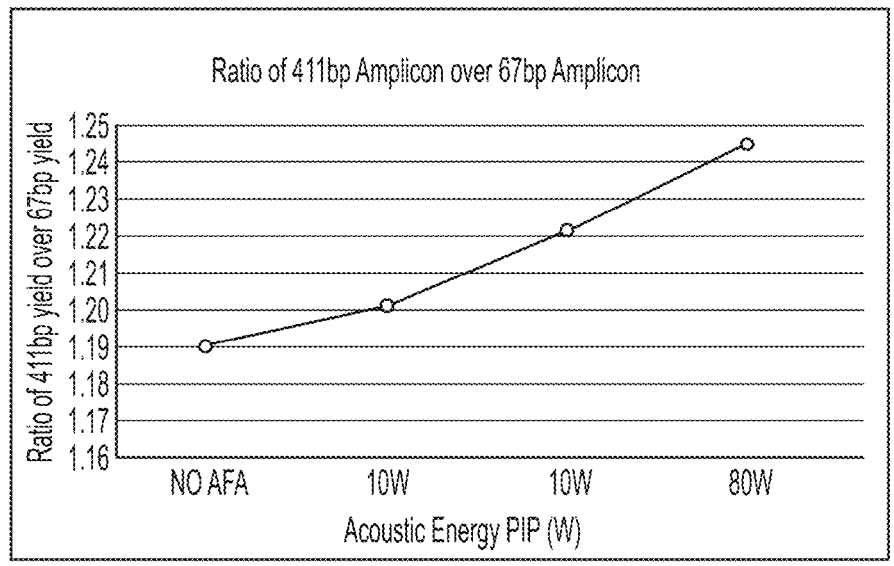
FIG. 4 shows the relationship of the ratio of the 411 bp/67 bp amplicon yield to acoustic treatment power for the yield analysis done in connection with FIG. 3.

The results of the qPCR assay shown in FIG. 3 indicated that while the 67 bp amplicon yield increased with processing energy, the 411 bp amplicon yield did not increase with processing energy. This is an indication that the use of focused acoustic energy does not release DNA from contaminating nucleated cells via lysis, but rather releases histone-bound DNA thereby increasing the availability of template for the 67 bp qPCR. While an argument might be made that the increase in the 67 bp amplicon yield is due to the slight reduction in the presence of the 411 bp amplicons as a result of focused acoustic energy shearing of the template for the 411 bp amplification, an analysis of the ratio of the yield of the 411 bp amplicon to the yield of the 67 bp amplicon does not support such an argument since the ratio of the 411 bp/67 bp also increases with the increased in focused acoustic energy power as shown in FIG. 4. If the increase in the 67 bp amplicon yield was due to the degradation of the 411 bp amplicon template, the ratio of the 411 bp/67 bp amplicon yield would have been similar in all dosage cases since the copy number of the template for the 411 bp amplicon does not change. FIG. 4 shows otherwise, however.

Figure 5:
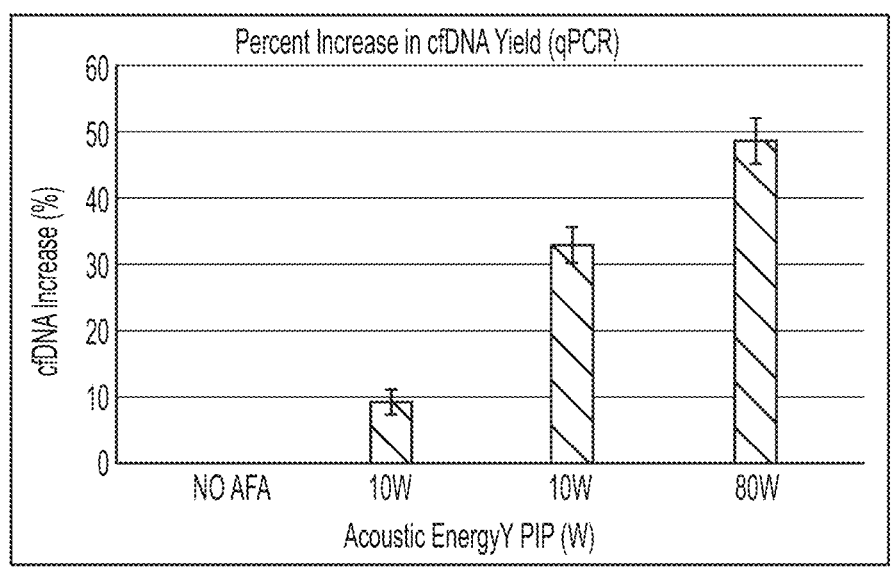
FIG. 5 shows the cfDNA yield for the samples in the yield analysis done in connection with FIG. 3.

Calculation of the percentage increase of the 67 bp amplicon yield, when corrected for the amplification of the 411 bp amplicon, indicates a significant increase in cfDNA yield with an increase in focused acoustic energy power as compared to the control sample that was not treated with focused acoustic energy, as shown in FIG. 5 below.

The ratio of low and high molecular weight cfDNA was shown to be important for diagnosis of cancer and monitoring of cancer treatment regimens (Umetani, N, et al. 2008. Prediction of Breast Tumor Progression by Integrity of Free Circulating DNA in Serum. J Clin Oncol 24:4270-4276). The DNA integrity index 20 data shown in FIG. 6 were obtained after extraction of cfDNA from Streck BCT plasma. Plasma was isolated as recommended from whole blood drawn from 18 healthy volunteers according to the manufacturer's protocol and as essentially described earlier (www.streck.com/resources/Cell_Stabilization/Cell-Free_DNA_BCT/01_Instructions_(IFU)/01_IFU_Cell-Free_DNA_BCT_IFU.pdf).

cfDNA was either isolated from 0.9 mL starting plasma using the Covaris truXTRAC-cfDNA from Plasma kit or from 0.5 mL plasma of the same donor with the QIAamp cfDNA isolation kit (Qiagen). The Covaris truXTRAC-cfDNA from Plasma protocol, but not the QIAamp cfDNA kit, employed an acoustic energy-based treatment step as described above (FIG. 3). qPCR was done on a 7500 Fast Real-Time 30 PCR instrument (ABI) as described below. PCR was performed in parallel presence of two different primer pairs that generate amplicons of human ALU repeats. Primer pair Alu115 is amplifying a 115 bp fragment of the human ALU repeat; primer pair Alu 247 is amplifying a 247 bp fragment. The primers are useful to assess the DNA integrity, expressed as a ratio of 247 bp over 115 bp fragments (in genome copy equivalent or normalized mass units) (Umetani, N, et al. 2008. Prediction of Breast Tumor Progression by Integrity of Free Circulating DNA in Serum. J Clin Oncol 5 24:4270-4276).

A serial dilution (5-6 orders of magnitude starting with 100,000 genome copy equivalents) of human gDNA (Promega, PN G3041) was used to generate a standard curve to calculate either genome copy equivalents or mass (in ng) of unknown input DNA (target). 15 µl of qPCR master mix containing AB Fast SYBR Green (Thermo, AB4385616) was mixed with 500 nM of each primer along with 5 µl of target. PCR conditions were as followed: 95° C. 1 min, followed by 35 cycles of 95° C. for 5 seconds, and annealing/extension at 62° C. for 30 seconds.

For direct comparison of yields obtained with truXTRAC cfDNA procedure to those obtained with the QIAamp cfDNA from Plasma kit (Qiagen, Hilden, Germany), qPCR was performed in parallel in the same 96-well plate.

The final yield is expressed in human genome copy equivalents or mass (ng) per ml of plasma. ALU repeat copy numbers of 1.1 million per human genome are used as a conversion factor to calculate human genome copy equivalents (Bennett, E A, et al. (2008. Active Alu retrotransposons in the human genome. Genome Research 18:1875-1883).

Figure 6:
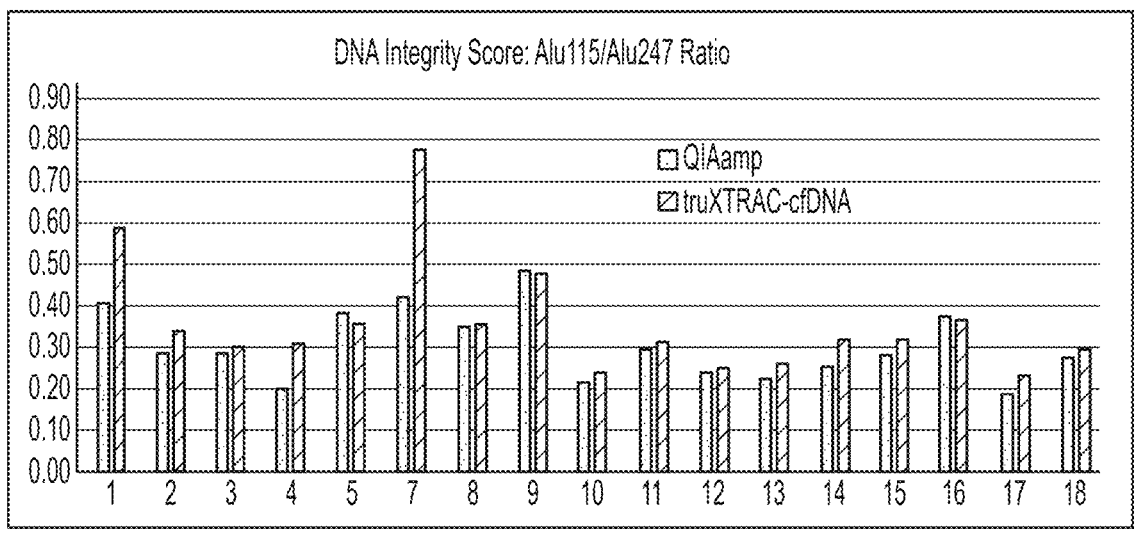
FIG. 6 shows fragment-size dependent quantitative human Alu-specific PCR analysis of cfDNAs isolated from Streck BCT plasma for multiple donors.

FIG. 6 shows the DNA integrity index expressed as the ratio of ALU247/ALU115 quantitation. The ratios obtained from truXTRAC-cfDNA eluates (i.e., data bars on the left side for each donor number) from donors #1, #4 and #7 show integrity indices that are significantly greater than those obtained after isolation via the QIAamp protocol (i.e., data bars on the right side for each donor number—the same donor plasma was used for each test). This is due to the presence of increased amounts of high molecular weight (>2 kb) DNA in the truXTRAC but not the QIAamp samples, which is reflected in the increase of the ALU247 amplicon yield. DNA from the nucleosomal small DNA fraction (fragment size peak at 165 bp) would not be amplifiable using the ALU247 primer pair due to simple fragment size constraints.

It is unlikely that the high molecular weight fraction is due to genomic DNA leaked from lysed white blood cells but this could only be proven by analyzing the sequence content of the two fractions (nucleosomal and high molecular weight). There are two mechanisms of cfDNA origination; apoptosis results in nucleosomal patterned DNA, whereas necrosis results in a more random mixture of DNA fragments with higher molecular weight (De Vlaminck, et al. 2014. Circulating Cell-Free DNA Enables Noninvasive Diagnosis of Heart Transplant Rejection. Sci Transl Med 6:241ra77). It is likely due to a QIAamp intrinsic kit/procedural characteristic that DNA with larger molecular weight is not being eluted from the QIAamp column matrix. The kit was originally designed for isolation of small viral genomic DNA and RNA.

Figure 7:
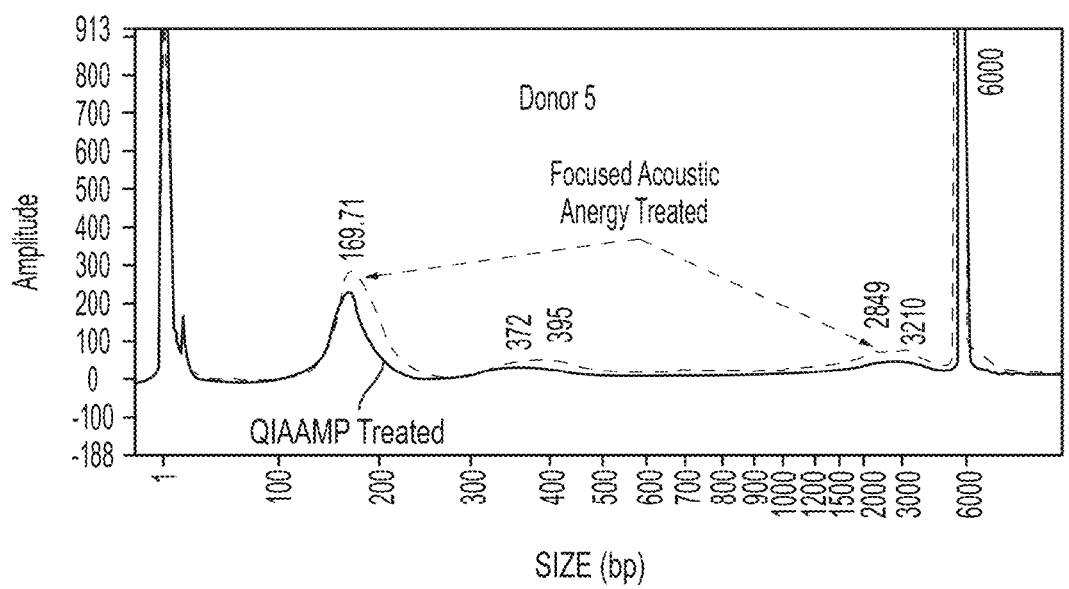
FIGS. 7 and 8 show cfDNA electropherogram profiles isolated from Streck BCT plasma for selected donors from FIG. 6.
Figure 8:
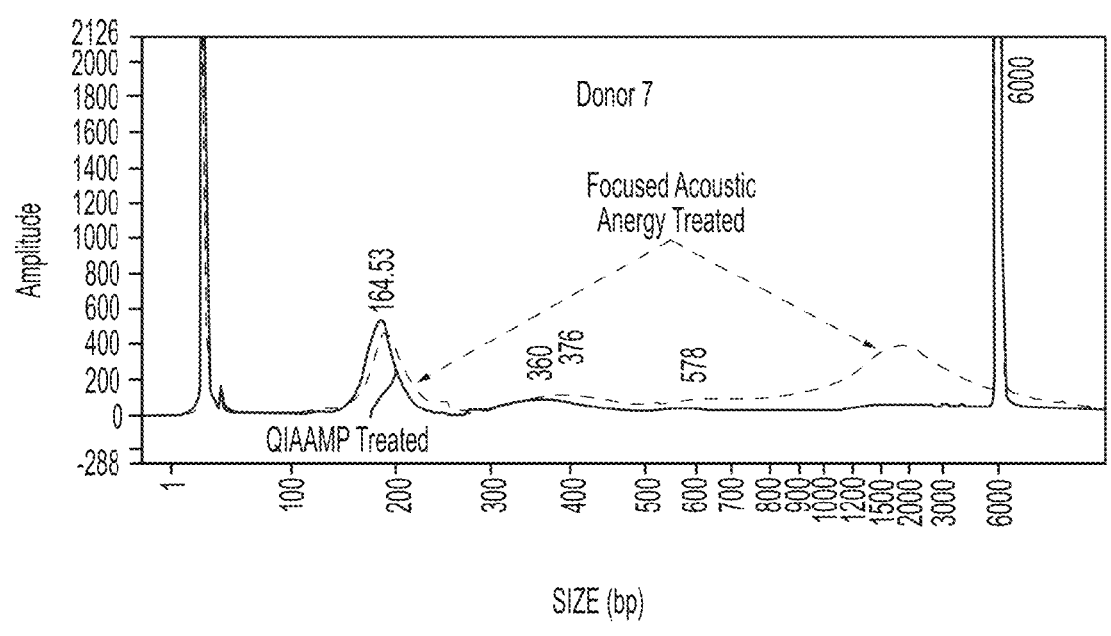

The DNA integrity indices are also mirrored in electropherograms of isolated cfDNA. Isolated cfDNA was analyzed by capillary electrophoresis (Fragment Analyzer, AATI, 48 Capillary System). The High Sensitivity NGS Fragment Analysis Kit (AATI, PN DNF-474) was used in conjunction with a longer injection time (90 seconds instead of 60 seconds) in order to increase sensitivity. A supplied base pair ladder was used to accurately determine fragment sizes. FIGS. 7 and 8 show electropherograms of isolated cfDNAs from donors 5 and 7, respectively. The cfDNA isolated from donor 7 plasma, but not that from donor 5 has a high ratio of high to low molecular weight DNA that is only present after treating the plasma with focused acoustic energy. The high molecular weight DNA is not present in the QIAamp purified cfDNA from this donor. Since it was shown that focused acoustic energy treatment does not change the DNA integrity due to lysis/release of DNA from contaminating cells (FIGS. 4 and 5), the origin of this high molecular weight DNA may be of significance for downstream analysis. That is, treatment with focused acoustic energy provides additional material for analysis that cannot be provided by the QIAamp process or other isolation methods that lack the focused acoustic treatment of plasma.

For certain stabilized or non-stabilized biological samples, current methods of biological sample extraction are also sub-optimal. For example, the high viscosity of sputum samples complicates their homogenization and use in standard molecular biology assays such as RT-qPCR for detection for respiratory viruses. FFPE-tissues and dried blood spots are examples of difficult-to-extract stabilized samples; in both cases, efficient re-hydration of the stabilized samples is needed for successful biomarker extraction. Treatment with focused acoustic energy can aid in re-hydration of such samples, as well as help release cfDNA from bound histones or other proteins. Thus, techniques described above can be used with different sample types, including samples that include non-fixed cfDNA (e.g., cfDNA that has not been treated with a fixing agent such as formaldehyde or similar material). In fact, the inventors have performed testing similar to that done above on samples that included non-stabilized cfDNA (collected from blood without using a fixing agent), and similar results were observed in that focused acoustic energy was shown to enhance extraction of cfDNA.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method for processing a sample containing a biomolecule to be recovered from the sample, comprising:
   providing an initial sample including cfDNA and whole cells;
   separating cfDNA from the whole cells in the initial sample to provide a sample containing cfDNA;
   providing the sample containing cfDNA that has histones and/or other proteins bound to the cfDNA in an acoustic treatment vessel;
   exposing the sample in the vessel to focused acoustic energy specifically adapted to remove or disrupt bonds between the cfDNA and bound histones and/or other proteins such that the specifically adapted focused acoustic energy alone acts to remove or disrupt bonds between the cfDNA and bound histones and/or other proteins without shearing of the cfDNA; and
   extracting the cfDNA from the sample after bonds between the cfDNA and bound histones and/or other proteins have been removed or disrupted by the focused acoustic energy;
   wherein the focused acoustic energy has a duty cycle of at least 5%, a 10 W to 80 W Peak Incident Power (PIP), and 50 cycles per burst for a processing time of 5 seconds to 120 seconds per sample.

2. The method of claim 1, wherein the sample containing cfDNA is previously chemically stabilized prior to being provided in the acoustic treatment vessel.

3. The method of claim 1, wherein the sample is a portion of a blood sample.

4. The method of claim 3, wherein the blood sample is chemically stabilized with a fixative.

5. The method of claim 3, wherein the sample includes serum separated from the blood sample by centrifugation.

6. The method of claim 1, wherein the acoustic treatment vessel is positioned in a fluid coupling medium that transmits the focused acoustic energy to the vessel.

7. The method of claim 1, wherein the step of exposing the sample in the vessel to focused acoustic energy includes moving a focal zone of the acoustic energy relative to the sample, and wherein a volume of the focal zone is less than a volume of the sample.

8. The method of claim 1, wherein the step of exposing the sample in the vessel to focused acoustic energy includes maintaining a focal zone of the acoustic energy stationary relative to the sample, and wherein a volume of the focal zone is larger than a volume of the sample.

9. The method of claim 1, wherein the sample is not chemically stabilized.

10. The method of claim 1, wherein the step of exposing enhances a reverse crosslinking rate of histones to the cfDNA.

11. The method of claim 1, wherein the step of exposing disrupts hydrogen bonding of histones or chaperone proteins to the cfDNA.

12. The method of claim 1, wherein bonds between cfDNA and bound histones and/or other proteins were created by chemical stabilization.

13. The method of claim 1, wherein the sample includes blood, spinal fluid, saliva, sputum, stool or urine.

14. The method of claim 1, wherein the sample is treated with a stabilization compound including a formaldehyde-providing compound or a disaccharide prior to being provided in the acoustic treatment vessel.

15. The method of claim 1, wherein the focused acoustic energy is generated by an acoustic energy source spaced from and exterior to the vessel, and the focused acoustic energy comprises a frequency of between about 100 kilohertz and about 100 megahertz and a focal zone having a width of less than about 2 centimeters.

16. The method of claim 15, wherein the acoustic energy source includes an acoustic transducer having a dome shape and arranged to generate focused acoustic energy to create the focal zone.

17. The method of claim 1, wherein the sample has a volume of 10 microliters to 150 milliliters.

\* \* \* \* \*